(12) United States Patent
Cao

(10) Patent No.: US 6,365,366 B1
(45) Date of Patent: Apr. 2, 2002

(54) T2K KINASE ASSAYS

(75) Inventor: Zhaodan Cao, South San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/524,435

(22) Filed: Mar. 13, 2000

(51) Int. Cl.[7] .......................... C12Q 1/42; C12Q 1/00; C12Q 1/48; G01N 33/53; A61K 38/00

(52) U.S. Cl. ..................... 435/21; 435/4; 435/968; 435/7.1; 435/15; 530/300

(58) Field of Search .................... 435/21, 4, 968, 435/7.1, 15; 530/300

(56) References Cited

FOREIGN PATENT DOCUMENTS

WO          99/01541      *  1/1999

* cited by examiner

*Primary Examiner*—Louise N. Leary
(74) *Attorney, Agent, or Firm*—Richard Aron Osman

(57) ABSTRACT

T2K kinase activity is detected by forming a mixture of a T2K kinase and a substrate; incubating the mixture under conditions whereby the kinase phosphorylates the substrate at a first rate; and detecting the first rate as an indication of the kinase activity. The substrate comprises $SX_1X_2X_3SX_4$ (SEQ ID NO:1) wherein $X_1$ and $X_4$ are aliphatic residues and both of the S residues are targets of the kinase, and especially, IKKα or IKKβ. In another embodiment, the mixture substrate comprises a particular IL-1 or TNF signaling cascade component. The mixture may be used to screen for agents which modulate the activity of the kinase, e.g. as an immuno-chemiluminescent assay.

17 Claims, No Drawings

T2K KINASE ASSAYS

FIELD OF THE INVENTION

The field of this invention is detecting the activity of an enzyme.

BACKGROUND

Inflammatory cytokines IL-1 and TNF exert diverse biological activities by altering gene expression in the cells, a function mediated in part by transcription factor NF-κB. In unstimulated cells, NF-κB proteins form a complex with inhibitory molecules, the IκB proteins, and are rendered inactive in the cytoplasm. In response to cytokines and other stimuli, the IκB proteins are phosphorylated on specific serine residues. Delineating TNF and IL-1 signaling pathways for NF-κB activation has implicated the TRAF molecules as converging point for different cytokines, with TRAF2 being involved in TNF- and TRAF6 in IL-1-induced NF-κB activation. We previously disclosed a family of IκB kinases including a TRAF2-associated kinase activity (designated T2K) and the translation product of the KIAA0151 gene product (also known as IKKi and IKKε) that phosphorylates the IκB molecules on the specific regulatory serine residues. We have now found that T2K and IKKi in fact have alternative substrate specificities and alternative physiologically relevant substrate targets, particularly IKKα and IKKβ peptide substrates. We disclose here materials and methods for assaying for these novel specificities.

RELEVANT LITERATURE

T2K (also known as TBK1) is described by Cao et al. (U.S. Pat. No. 5,776,717) and Pomerantz and Baltimore, EMBO J. 18 (23), 6694–6704, 1999; Genbank Accession No. NM_013254 and NP_037386 (human); AF191839 and AAF05990.1 (mouse).

IKKi is described by Nagase et al., DNA Res.,1995, 2, 167–174; Genbank Accession Nos. D63485 and BAA09772 (human); and by Shimada et al., Int Immunol. 1999 Aug;11 (8):1357–62; Genbank Accession Nos.AB016590 and BAA85155.1 (human); AB016589 and BAA85154.1 (mouse).

IKKα is described in Regnier et al. 1997, Cell 90, 373–383; Genbank Accession Nos.AF012890 and AAC51662.1 (human).

IKKβ is described in U.S. Pat. No. 5,939,302; Genbank Accession Nos.AF029vand AAC51860.1 (human).

Song et al., U.S. Pat. No. 5,874,230 disclose a TRAF2-associated kinase.

SUMMARY OF THE INVENTION

The invention provides compositions and methods for detecting kinase activity. The subject compositions include in vitro mixtures comprising or consisting essentially of an isolated, active T2K kinase and an isolated, functional T2K substrate. In one embodiment, the substrate comprises or consists essentially of $SX_1X_2X_3SX_4$ (SEQ ID NO:1) wherein $X_1$ and $X_4$ are aliphatic residues and both of the S residues are targets of the kinase. In particular aspects, $X_1$ and $X_4$ are L and F, respectively; $X_1$–$X_4$ are L, C, T and F, respectively; the substrate comprises a sequence selected from the group consisting of YAKDVDQGSLCTS-FVGTLQYL (SEQ ID NO:2) and YAKELDQGSLCTS-FVGTLQYL (SEQ ID NO:3); and/or the substrate comprises a natural human kinase selected from the group consisting of IKKα and IKKβ. In another embodiment, the substrate comprises or consists essentially of an IL-1 or TNF signaling cascade component selected from the group consisting of: an isolated natural human IL-1 Rc superfamily receptor selected from the group consisting of IL-1RP1, IL-1RP2, IL-1RP3, IL-18Rc, and TLR2 and TLR4; natural human NfκB protein selected from the group consisting of p50, p65, p49, cRel and RelB; a natural human protein selected from the group consisting of I-TRAF and IKKγ; a natural human protein selected from the group consisting of TRAF5 and TRAF6; a natural human protein selected from the group consisting of RIP, IRAK, MYD88 and TRADD; and a natural human TNFRc1 protein selected from the group consisting of CD40 and CD30.

The subject methods for detecting kinase activity comprise the steps of forming a subject mixture, incubating the mixture under conditions whereby the kinase phosphorylates the substrate at a first rate, and detecting the first rate as an indication of the kinase activity. In particular aspects, the mixture comprises an agent and but for the presence of the agent, the kinase phosphorylates the substrate at a second rate, wherein a significant difference between the first and second rate is an indication that the agent modulates the kinase activity. In more particular aspects, the detecting step is a chemiluminescent assay comprising detecting the phosphorylated substrate with a specific, labeled probe, particularly wherein the phosphorylated substrate is immobilized and detecting the phosphorylated substrate is effected indirectly by detecting a substrate-specific primary antibody with the probe, wherein the probe is a labeled secondary antibody specific for the primary antibody.

DETAILED DESCRIPTION OF THE INVENTION

The invention provides a method for detecting kinase activity comprising the steps of (a) forming a mixture comprising an active T2K kinase and a T2K substrate; (b) incubating the mixture under conditions whereby the kinase phosphorylates the substrate at a first rate; and (c) detecting the first rate as an indication of the kinase activity. As used herein, the term T2K kinase describes the two related natural proteins T2K and natural IKKi, however insubstantial variants such as minor truncations, etc. which retain substantially the same kinase activity and specificity of the native proteins are clearly equivalents in the disclosed assays. The T2K kinases may be produced recombinantly and/or isolated from any convenient source, particularly human or murine cells, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY).

The T2K substrate is of sufficient length and sequence to provide a functional substrate for the T2K kinase under assay conditions. Depending on the assay structure, the substrate is generally a peptide of at least 5, preferably at least 10, more preferably at least 15 residues in length. In many cases, cost and specificity are optimized by using peptides of fewer than 100 residues, preferably fewer than 50 residues, more preferably fewer than 25 residues, as opposed to native protein substrates.

In one embodiment, the T2K substrate comprises $SX_1X_2X_3SX_4$ (SEQ ID NO:1), wherein $X_1$ and $X_4$ are aliphatic residues and both of the S residues are targets of the kinase, particularly wherein $X_1$ and $X_4$ are L and F, more particularly wherein $X_1$–$X_4$ are L, C, T and F, respectively. Table 1 provides exemplary peptides providing requisite T2K substrate specificity.

Table 1. Exemplary peptides providing requisite T2K substrate specificity.

| Peptide | Sequence Identifier | T2K substrate specificity |
|---|---|---|
| GGSLCTSF | (SEQ ID NO:4) | +++ |
| GGSLMTSF | (SEQ ID NO:5) | +++ |
| GGSFCTSL | (SEQ ID NO:6) | +++ |
| DQGSFCTSL | (SEQ ID NO:7) | +++ |
| VDQGSLAASFVGT | (SEQ ID NO:8) | +++ |
| VDQGSMAASLVGT | (SEQ ID NO:9) | +++ |
| VDQGSIAASFVGT | (SEQ ID NO:10) | +++ |
| AKDVDQGSVCTSFVGTLQY | (SEQ ID NO:11) | +++ |
| AKDVDQGSLCTSLVGTLQY | (SEQ ID NO:12) | +++ |
| AKDVDQGSFCTSLVGTLQY | (SEQ ID NO:13) | +++ |

In more particular embodiments the substrate comprises an IKKα fragment including serines 176 and 180 or an IKKβ fragment including serines 177 and 181; hence, there are ten IKKα fragments and ten IKKβ fragments 15 residues in length (IKKβ resides 167–181, 168–182, etc.). Particular substrates include IKKα fragment YAKDVDQGSLCTS-FVGTLQYL (SEQ ID NO:2) and IKKβ fragment YAKELDQGSLCTSFVGTLQYL (SEQ ID NO:3). Alternatively, native IKKα and IKKβ substrates may be used.

In another embodiment, the T2K substrate comprises an IL-1 or TNF signaling cascade component other than IκB and TRAF2, such as a natural human IL-1Rc superfamily receptor selected from the group consisting of IL-1RP1, IL-1RP2, IL-1RP3, IL-18Rc, TLRC2 and TLR4; a natural human NfκB protein selected from the group consisting of p50, p65, p49, cRel and RelB; a natural human protein selected from the group consisting of I-TRAF and IKKγ (also known as NEMO); a natural human protein selected from the group consisting of TRAF5 and TRAF6; a natural human protein selected from the group consisting of RIP, IRAK, MYD88 and TRADD; and a natural human TNFRc1 protein selected from the group consisting of CD40 and CD30. These enumerated components are all defined in the art and readily isolated or produced recombinantly using sequence available through public repositories such as Genbank. In addition, insubstantial variants such as minor truncations, etc. which retain substantially the same kinase activity and specificity of the native proteins are clearly equivalents in the disclosed assays.

After forming the mixture, the method involves incubating the mixture under conditions whereby the kinase phosphorylates the substrate at a first rate; and detecting the first rate as an indication of the kinase activity. Incubation conditions and periods are for kinase activity but also minimized to facilitate rapid, high-throughput screening. For continuous assays, the rate may be expressed in terms of a dynamic activity, whereas in most applications, the assays are discontinuous (e.g. have a fixed-time endpoint) so the rate is expressed as net kinase activity over a fixed time.

In a particular embodiment, the method is used to screen for agents which modulate the activity of the kinase, wherein the mixture comprises an agent and but for the presence of the agent, the kinase phosphorylates the substrate at a second rate, wherein a significant difference between the first and second rate is an indication that the agent modulates the kinase activity. A wide variety of homogeneous and heterogeneous (solid phase) assays may be used, including fluorescent polarization assays, homogeneous time resolved fluorescence assays (HTRF), capture assays such as described by Strulovici in U.S. Pat. No. 5,759,787, etc. In particular embodiments, the detecting step is a chemiluminescent assay comprising detecting the phosphorylated substrate with a specific, labeled probe, particularly wherein the phosphorylated substrate is immobilized and detecting the phosphorylated substrate is effected indirectly by detecting a substrate-specific primary antibody with the probe, wherein the probe is a labeled secondary antibody specific for the primary antibody.

The following experimental section and examples are offered by way of illustration and not by way of limitation.

EXAMPLES

1. Chemiluminescent Protein Kinase Assay
A. Materials:
   1) Recombinant human T2K purified from baculovirus infected insect cells
   2) Substrate: biotinylated peptide (SEQ ID NO:2)
   3) Streptavidin coated microtiter plates: coated in-house
   4) Primary antibody: anti-phosphoserine mAb, specific for epitope
   5) Secondary antibody: HRP conjugated goat anti-mouse antibody
   6) SuperSignal detection reagent B. Methods:
Plate Coating:
   1) Reconstitute streptavidin directly from powder in PBS at around 40 μg/ml and coat Dynatech Microlite-2 plates (120 μl/well) either O/N at 4° C. or 2 hr RT. The plate can be stored at 4° C. for at least 3 days with no loss of binding capacity. Directly before use wash the plate 3× with 200 μl d.w.

Kinase Reaction:
   2) Reaction mixture contains in a final volume of 90 μl/well: 20 mM Tris-HCl, pH 7.5, 10 mM $MgCl_2$, 2 mM EDTA, 1 mM NaF, 0.5 mM benzamidine, 1 mM DTT, 0.1% NP-40, 100 μM ATP, $1\times10^{-6}$ M substrate.

3) Add test compound: 10 µl/well in DMSO.
4) Add enzyme in 10 µl buffer containing Tris-HCl pH 7.5 20 mM, 10 % DMSO, EDTA 2 mM, benzamidine 2 mM, DTT 1 mM, NP-40 0.1%, MgCl$_2$ 1 mM.
5) Incubate at room temperature for 40 min.

ELISA Reaction:
6) Wash 3× with 300 µl PBS.
7) Add 100 µl/well primary antibody (1:10,000) premixed with secondary antibody (1:5,000) in PBS containing 2% BSA. Incubate at room temperature for 40 min on shaker.
8) Wash 3× with 300 µl PBS.

Detection:
9) Add 100 µl/well 3× diluted SuperSignal substrate. Incubate at RT for 10 min and read by luminometer.

2. Continuous High-Throughput In Vitro Fluorescence Polarization Assay

Sensor: Rhodamine-labeled peptide (SEQ ID NO:3, final conc.=1–5 nM)
Kinase: T2K (final conc.=100–200 nM)
Buffer: 10 mM HEPES, 10 mM NaCl, 6 mM magnesium chloride, pH 7.6

1. Add 90 microliters of Sensor/Kinase mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

3. Solid Phase IKKi Phosphorylation Assay

A. Reagents:
Neutralite Avidin: 20 µg/ml in PBS.
kinase: $10^{-8}$–$10^{-5}$M IKKi at 20 µg/ml in PBS.
substrate: $10^{-7}$–$10^{-4}$M biotinylated substrate (SEQ ID NO:13) at 40 µg/ml in PBS.
Blocking buffer: 5% BSA, 0.5% Tween 20 in PBS; 1 hour at room temperature.
Assay Buffer: 100 mM KCl, 10 mM MgCl$_2$, 1 mM MnCl$_2$, 20 mM HEPES pH 7.4, 0.25 mM EDTA, 1% glycerol, 0.5% NP-40, 50 mM BME, 1 mg/ml BSA, cocktail of protease inhibitors.
[$^{32}$P]γ-ATP 10× stock: $2\times10^{-5}$M cold ATP with 100 µCi [$^{32}$P]γ-ATP. Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of Assay Plates
Coat with 120 µl of stock N Avidin per well overnight at 4° C.
Wash 2 times with 200 µl PBS.
Block with 150 µl of blocking buffer.
Wash 2 times with 200 µl PBS.

C. Assay
Add 40 µl assay buffer/well.
Add 40 µl biotinylated substrate (2–200 pmoles/40 ul in assay buffer)
Add 40 µl kinase (0.1–10 pmoles/40 ul in assay buffer)
Add 10 µl compound or extract.
Add 10 µl [$^{32}$P]γ-ATP 10× stock.
Shake at 25° C. for 15 minutes.
Incubate additional 45 minutes at 25° C.
Stop the reaction by washing 4 times with 200 µl PBS.
Add 150 µl scintillation cocktail.
Count in Topcount.

D. Controls for all Assays (Located on Each Plate)
a. Non-specific binding
b. cold ATP at 80% inhibition.

4. Solid Phase T2K Phosphorylation Assay

A. Reagents
Neutralite Avidin: 20 µg/ml in PBS.
kinase: $10^{-8}$–$10^{-5}$M T2K (residues 1–728) at 20 µg/ml in PBS.
substrate: $10^{-7}$–$10^{31\ 4}$Mbiotinylated substrate (SEQ ID NO:3) at 40 µg/ml in PBS.
Blocking buffer: 5% BSA, 0.5% Tween 20 in PBS; 1 hour at room temperature.
Assay Buffer: 100 mM KCl, 10 mM MgCl$_2$, 1 mM MnCl$_2$, 20 mM HEPES pH 7.4, 0.25 mM EDTA, 1% glycerol, 0.5% NP-40, 50 mM BME, 1 mg/ml BSA, cocktail of protease inhibitors.
[$^{32}$P]γ-ATP 10× stock: $2\times10^{-5}$M cold ATP with 100 µCi [$^{32}$P]γ-ATP. Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of Assay Plates
Coat with 120 µl of stock N Avidin per well overnight at 4° C.
Wash 2 times with 200 µl PBS.
Block with 150 µl of blocking buffer.
Wash 2 times with 200 µl PBS.

C. Assay
Add 40 µl assay buffer/well.
Add 40 µl biotinylated substrate (2–200 pmoles/40 ul in assay buffer)
Add 40 µl kinase (0.1–10 pmoles/40 ul in assay buffer)
Add 10 µl compound or extract.
Add 10 µl [$^{32}$P]γ-ATP 10× stock.
Shake at 25° C. for 15 minutes.
Incubate additional 45 minutes at 25° C.
Stop the reaction by washing 4 times with 200 µl PBS.
Add 150 µl scintillation cocktail.
Count in Topcount.

D. Controls for all Assays (Located on Each Plate)
a. Non-specific binding
b. cold ATP at 80% inhibition.

3. Protocol for high throughput T2K-TRAF2 heterodimer formation assay

A. Reagents
Neutralite Avidin: 20 µg/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.
$^{33}$P T2K protein 10× stock: $10^{-8}$–$10^{-6}$M "cold" T2K supplemented with 200,000–250,000 cpm of labeled T2K (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

TRAF2: $10^{-7}$–$10^{-5}$M biotinylated TRAF2 in PBS.

B. Preparation of Assay Plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-T2K (20–25,000 cpm/0.1–10 pmoles/well= $10^{-9}$–$10^{-7}$ M final conc).

Shake at 25° C. for 15 minutes.

Incubate additional 45 minutes at 25° C.

Add 40 μl biotinylated TRAF2 (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all Assays (Located on Each Plate)

a. Non-specific binding b. Soluble (non-biotinylated TRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting kinase activity comprising the steps of:
    (a) forming a mixture comprising an active T2K kinase and a T2K substrate comprising $SX_1X_2X_3SX_4$ (SEQ ID NO:1), wherein $X_1$ and $X_4$ are aliphatic residues and both of the S residues are targets of the kinase;
    (b) incubating the mixture under conditions whereby kinase phosphorylates the substrate at a first rate; and
    (c) detecting the first rate as an indication of the kinase activity.

2. The method according to claim 1, wherein $X_1$ and $X_4$ are aliphatic residues and both of the S residues are targets of the kinase.

3. The method according to claim 1, wherein $X_1$ and $X_4$ are L and F.

4. The method according to claim 1, wherein $X_1$–$X_4$ are L, C, T and F, respectively.

5. The method according to claim 1, wherein the substrate comprises a sequence selected from the group consisting of YAKDVDQGSLCTSFVGTLQYL (SEQ ID NO:2) and YAKELDQGSLCTSFVGTLQYL (SEQ ID NO:3).

6. The method according to claim 1, wherein the substrate comprises a natural human kinase selected from the group consisting of IKKα and IKKβ.

7. The method according to claim 1, wherein the mixture comprises an agent and but for the presence of the agent, the kinase phosphorylates the substrate at a second rate, wherein a significant difference between the first and second rate is an indication that the agent modulates the kinase activity.

8. The method according to claim 1, wherein the detecting step is a chemiluminescent assay comprising detecting the phosphorylated substrate with a specific, labeled probe.

9. The method according to claim 1, wherein the detecting step is a chemiluminescent assay comprising detecting the phosphorylated substrate with a specific, labeled probe, wherein the phosphorylated substrate is immobilized and detecting the phosphorylated substrate is effected indirectly by detecting a substrate-specific primary antibody with the probe, wherein the probe is a labeled secondary antibody specific for the primary antibody.

10. The method according to claim 1, wherein the mixture comprises an agent and but for the presence of the agent, the kinase phosphorylates the substrate at a second rate, wherein a significant difference between the first and second rate is an indication that the agent modulates the kinase activity.

11. The method according to claim 1, wherein the detecting step is a chemiluminescent assay comprising detecting the phosphorylated substrate with a specific, labeled probe.

12. The method according to claim 1, wherein the detecting step is a chemiluminescent assay comprising detecting the phosphorylated substrate with a specific, labeled probe, wherein the phosphorylated substrate is immobilized and detecting the phosphorylated substrate is effected indirectly by detecting a substrate-specific primary antibody with the probe, wherein the probe is a labeled secondary antibody specific for the primary antibody.

13. The method according to claim 4, wherein the detecting step is a chemiluminescent assay comprising detecting the phosphorylated substrate with a specific, labeled probe, wherein the phosphorylated substrate is immobilized and detecting the phosphorylated substrate is effected indirectly by detecting a substrate-specific primary antibody with the probe, wherein the probe is a labeled secondary antibody specific for the primary antibody.

14. A method for detecting kinase activity comprising the steps of:
    (a) forming a mixture comprising an active T2K kinase and a T2K substrate comprising an IL-1 or TNF signaling cascade component selected from the group consisting of:
        a natural human IL-1Rc superfamily receptor selected from the group consisting of IL-1RP1, IL-1RP2, IL-1RP3, IL-18Rc, TLR2 and TLR4;
        a natural human NfκB protein selected from the group consisting of p50, p65, p49, cRel and RelB;
        a natural human protein selected from the group consisting of I-TRAF and IKKγ;
        a natural human protein selected from the group consisting of TRAF5 and TRAF6;
        a natural human protein selected from the group consisting of RIP, IRAK, MYD88 and TRADD; and
        a natural human TNFRc1 protein selected from the group consisting of CD40 and CD30;
    (b) incubating the mixture under conditions whereby the kinase phosphorylates the substrate at a first rate; and
    (c) detecting the first rate as an indication of the kinase activity.

15. The method according to claim 14, wherein the mixture comprises an agent and but for the presence of the agent, the kinase phosphorylates the substrate at a second rate, wherein a significant difference between the first and second rate is an indication that the agent modulates the kinase activity.

16. The method according to claim 14, wherein the detecting step is a chemiluminescent assay comprising detecting the phosphorylated substrate with a specific, labeled probe.

17. The method according to claim 14, wherein the detecting step is a chemiluminescent assay comprising detecting the phosphorylated substrate with a specific, labeled probe, wherein the phosphorylated substrate is immobilized and detecting the phosphorylated substrate is effected indirectly by detecting a substrate-specific primary antibody with the probe, wherein the probe is a labeled secondary antibody specific for the primary antibody.

* * * * *

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial  Sequence: Synthetic
      Sequence
<220> FEATURE:
<221> NAME/KEY: VARIANT
<222> LOCATION: (2)..(6)
<223> OTHER INFORMATION: First and fourth Xaa represent aliphatic
      residues; second and third Xaa r epresent any amino acid.

<400> SEQUENCE: 1

Ser Xaa Xaa Xaa Ser Xaa
 1               5

<210> SEQ ID NO 2
<211> LENGTH: 21
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 2

Tyr Ala Lys Asp Val Asp Gln Gly Ser Leu C ys Thr Ser Phe Val Gly
 1               5                  10                  15

Thr Leu Gln Tyr Leu
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 3
```

Tyr Ala Lys Glu Leu Asp Gln Gly Ser Leu Cys Thr Ser Phe Val Gly
 1               5                  10                 15

Thr Leu Gln Tyr Leu
            20

<210> SEQ ID NO 4
<211> LENGTH: 8
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 4

Gly Gly Ser Leu Cys Thr Ser Phe
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 5

Gly Gly Ser Leu Met Thr Ser Phe
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 6

Gly Gly Ser Phe Cys Thr Ser Leu
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 7

Asp Gln Gly Ser Phe Cys Thr Ser Leu
 1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial  Sequence: Synthetic
      Sequence

<400> SEQUENCE: 8

```
Val Asp Gln Gly Ser Leu Ala Ala Ser Phe Val Gly Thr
 1               5                  10
```

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 9

```
Val Asp Gln Gly Ser Met Ala Ala Ser Leu Val Gly Thr
 1               5                  10
```

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 10

```
Val Asp Gln Gly Ser Ile Ala Ala Ser Phe Val Gly Thr
 1               5                  10
```

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 11

```
Ala Lys Asp Val Asp Gln Gly Ser Val Cys Thr Ser Phe Val Gly Thr
 1               5                  10                  15

Leu Gln Tyr
```

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 12

```
Ala Lys Asp Val Asp Gln Gly Ser Leu Cys Thr Ser Leu Val Gly Thr
 1               5                  10                  15

Leu Gln Tyr
```

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 13

```
Ala Lys Asp Val Asp Gln Gly Ser Phe Cys Thr Ser Leu Val Gly Thr
 1               5                  10                  15

Leu Gln Tyr
```